United States Patent

Parekh et al.

[11] Patent Number: 5,718,876
[45] Date of Patent: Feb. 17, 1998

[54] BASIC ALUMINUM AND ALUMINUM/ZIRCONIUM ANTIPERSPIRANTS AND METHOD OF MAKING THE SAME

[75] Inventors: Jawahar C. Parekh, Livingston; Andrew M. Rubino, New Providence, both of N.J.

[73] Assignee: Reheis Inc., Berkley Heights, N.J.

[21] Appl. No.: 635,290

[22] Filed: Apr. 19, 1996

Related U.S. Application Data

[63] Continuation of Ser. No. 579,902, Sep. 7, 1990, abandoned.

[51] Int. Cl.$^6$ ............... C01B 7/00; A61K 7/38; A61K 7/34
[52] U.S. Cl. ............... 423/462; 424/65; 424/66; 424/68
[58] Field of Search ............... 423/462; 424/65, 424/66, 68

[56] References Cited

U.S. PATENT DOCUMENTS

| | | | |
|---|---|---|---|
| 3,891,745 | 6/1975 | Bellan et al. | 423/462 |
| 3,904,741 | 9/1975 | Jones et al. | 423/462 |
| 3,947,556 | 3/1976 | Jones et al. | 423/462 |
| 3,947,557 | 3/1976 | Jones et al. | 423/462 |
| 3,957,947 | 5/1976 | Yamada et al. | 423/462 |
| 4,017,599 | 4/1977 | Rubino | 424/47 |
| 4,359,456 | 11/1982 | Gosling et al. | 424/68 |
| 4,775,528 | 10/1988 | Callaghan et al. | 424/66 |
| 4,818,512 | 4/1989 | Markarian et al. | 423/462 |
| 4,859,446 | 8/1989 | Arbutyn et al. | 423/462 |
| 4,944,933 | 7/1990 | Inward | 423/462 |

FOREIGN PATENT DOCUMENTS

| | | |
|---|---|---|
| 0 191 628 A2 | 8/1986 | European Pat. Off. |
| 0 256 831 A2 | 2/1988 | European Pat. Off. |
| 0 256 832 A2 | 2/1988 | European Pat. Off. |
| 0 274 252 A1 | 7/1988 | European Pat. Off. |
| 2 018 590 A | 10/1979 | United Kingdom |

*Primary Examiner*—Shelley A. Dodson
*Attorney, Agent, or Firm*—Panitch Schwarze Jacobs & Nadel, P.C.

[57] ABSTRACT

Basic aluminum halides and nitrates having enhanced antiperspirant efficacy are produced by reacting (a) aluminum powder, (b) an aluminum halide or nitrate solution and (c) water at a temperature greater than about 85° C. This reaction is maintained until reaction products having an Al:anion ratio of about 1.2 to 1.8 and a solution solids concentration of about 30–40 wt. % on an anhydrous basis are obtained. The products are characterized as having a Size Exclusion Chromatography Test Band having a relative retention time corresponding to Band II of a Standard Basic Aluminum Chloride Size Exclusion Chromatogram and a Band II percent aluminum value of at least about 50% and a Band III percent aluminum value of less than 20%.

10 Claims, No Drawings

BASIC ALUMINUM AND ALUMINUM/ZIRCONIUM ANTIPERSPIRANTS AND METHOD OF MAKING THE SAME

CROSS-REFERENCE TO RELATED APPLICATIONS

This application is a continuation of U.S. patent application Ser. No. 07/579,902, filed on Sep. 7, 1990 now abandoned.

FIELD OF THE INVENTION

The present invention relates to the production of basic aluminum compounds and aluminum/zirconium compounds and complexes. More importantly, the invention is directed to basic aluminum halides and nitrates and basic aluminum halide or nitrate/zirconium complexes having antiperspirant efficacy.

BACKGROUND OF THE INVENTION

Basic aluminum halides and nitrates, particularly chlorides, and their use as effective antiperspirant compounds are both well-known. In general, basic aluminum halides and nitrates are complex structures made up of mixtures of polymeric and monomeric species of various sizes and molecular structures, depending upon their Al:anion ratio, together with varying amounts of bound or coordinated water. The basic aluminum compounds are generally represented by the empirical formula:

$$Al_2(OH)_{(6-x)}Y_x$$

wherein Y is Cl, Br, I and/or $NO_3$, and x may be between 0 and 6. It should be understood that the above formula is greatly simplified and is intended to include basic aluminum halides and nitrates containing coordinated or bound molecules of water as well as basic aluminum halide and nitrate polymer complexes and mixtures of the above.

Many attempts have been made to improve the antiperspirant efficacy and other properties of basic aluminum compounds. One school of thought that has grown in popularity is based upon improving the efficacy of basic aluminum compounds by increasing the percentage of aluminum species having a retention time corresponding to Band III of a Standard Basic Aluminum Chloride Size Exclusion Chromatogram. A number of attempts to increase efficacy have focused on processes for the production of such basic aluminum compounds.

For example, U.S. Pat. No. 4,359,456 of Gosling et al. (Unilever) discloses heating a wide range of basic aluminum halides and nitrates in a 10 to 34 wt. % aqueous solution (2.5 to 8.5 wt. % aluminum) to a temperature of 50° to 140° C. for a period of time sufficient to cause the basic aluminum compound to have a Size Exclusion Chromatography Test Band having a relative retention time corresponding to Band III and a Band III aluminum value of at least 20%. The heating step is carried out for a period of from ½ hour to 30 days in a closed tube, bottle or reactor, followed by cooling to ambient temperature and drying to a water soluble powder. The increase of the percentage of aluminum in the Band III fraction to a level of 20% or more is said to result in an enhancement of the antiperspirant activity of the basic aluminum compound.

U.S. Pat. No. 4,775,528 of Callaghan et al. (Gillette) discloses an antiperspirant composition of zirconyl hydroxy chloride and aluminum hydroxide in a stable solid. Enhanced efficacy is reportedly achieved by heating a 2% to 20% by weight aqueous solution, containing at least the aluminum chlorhydroxide component of the composition, until the ratio of the height of the peak corresponding to Kd=0.7 (Band IV) to that of the peak corresponding to Kd=0.5 (Band III) is at least 2:1. At column 2, lines 60–61 of this patent it is disclosed that at least 80% and preferably at least 90% of the total of aluminum is present within the peaks corresponding to Bands III and IV.

U.S. Pat. No. 4,944,933 of Inward (Unilever) discloses a process for the manufacture of basic aluminum chlorides in powder form for antiperspirant use in which an Al:Cl molar ratio of 1.7:1 to 2.2:1 and a Band III fraction of at least 20% is obtained. The process of this patent comprises dissolving metallic aluminum powder in an aqueous starting solution of aluminum chloride or basic aluminum chloride having an Al:Cl molar ratio of up to 1.8:1. The starting solution is held at a temperature of about 50° C. to about 105° C. for a period long enough to dissolve sufficient aluminum to produce an aqueous solution having an Al:Cl molar ratio in the range of 1.7 to 2.2:1 and an aluminum concentration of 7.5 to 13% by weight. The reaction is carried out in such a manner so that the aluminum powder is dissolved rapidly enough so that the final basic aluminum chloride has a Band III fraction of at least 20%, preferably 25%. The solution is then dried to provide a final basic aluminum chloride in a form of a hydrated powder having a Band III fraction of at least 20%, preferably 25%.

European Published Patent Applications Nos. 0 191 628 and 0 256 832 of Unilever disclose the preparation of basic aluminum halides having at least 20% of the aluminum contained in the Band III fraction for use in antiperspirants. These references disclose processes for the direct manufacture of basic aluminum halides having an aluminum/halide molar ratio of 1.7:1 to 2.2:1 from the known reaction of aluminum metal with aluminum halides. The processes require a reaction temperature of from 50° to 105° C. The final aluminum concentration of the solutions is 0.8% to 6.75%. The solutions may be dried to provide a powder.

European Patent Application No. 0 274 252 of Dow discloses a process for preparing basic aluminum compounds which have a Band III percent aluminum value of at least 40%. The process comprises reacting an aluminum compound of a prescribed formula with aluminum metal in an aqueous medium at a temperature of between 50° C. to 195° C. until a ratio of aluminum to anion of 0.5 to 2.5:1 is obtained.

Antiperspirant compositions comprising combinations of aluminum compounds and zirconium compounds or complexes are also known in the art. For example, U.S. Pat. No. 4,017,599 of Rubino (Armour Pharmaceutical) discloses water soluble complexes of a basic aluminum compound, a zirconium compound and an amino compound. The products have an Al/Zr molar ratio of about 10:1 to 1:10. European Published Patent Application No. 0 256 831 of Unilever discloses a process for the manufacture of aluminum zirconium halohydrates, having an Al/Zr ratio of 2:1 to 7:1. The process comprises dissolving metallic aluminum halide in a zirconium-halide mixture heated to 50° to 105° C. The final product has a size exclusion chromatogram of which the Band III portion is at least 20%.

However, such basic aluminum and aluminum zirconium compounds having a preponderance of Band III aluminum species and processes for the production of such compounds have proven to have a number of disadvantages, particularly in their preparation. For example, these processes generally require high heating temperatures to properly modify the basic aluminum species. This high degree of heating raises the cost of manufacturing these compounds. Moreover, in order to increase the concentration of the Band III species, relatively low concentration solutions of the starting materials need to be employed. This raises the cost of drying the solutions to powders. Also, basic aluminum compounds having a high percentage of Band III are relatively unstable in aqueous solutions at room temperature.

BRIEF SUMMARY OF THE INVENTION

According to the present invention, basic aluminum halides and nitrates may be prepared by reacting (a) an aluminum powder, (b) an aluminum halide or nitrate solution and (c) water. The components are reacted at a temperature greater than about 85° C. The reaction is maintained until reaction products having an Al:anion ratio of about 1.2 to about 1.8 and a solution solids concentration of about 28 to about 42 wt. % on an anhydrous basis are obtained. The reaction product is characterized as having a Size Exclusion Chromatography Test Band having a relative retention time corresponding to Band II of a Standard Basic Aluminum Chloride Size Chromatogram and having a Band II percent aluminum value of at least about 50% and a Band III percent aluminum value of less than 20%. Preferably, the products also have a Band I percent aluminum value of less than about 1%.

The present invention also encompasses a method of preparing aluminum halide and nitrate zirconium complexes. The zirconium compounds are preferably buffered with amino acid. The method for preparing these compounds comprises reacting, at room temperature, a basic aluminum halide or nitrate solution produced in accordance with the present method, with a zirconium compound or a zirconium/amino acid complex. The zirconium/amino acid complex is preferably prepared by refluxing a zirconium compound with an amino acid for about 4 hours to form a reaction product.

The present processes for preparing basic aluminum halides and nitrates having a preponderance of aluminum species in Band II and aluminum halide and nitrate/zirconium complexes of these compounds overcome the disadvantages of the prior art, as well as demonstrate excellent efficacy. The basic aluminum halides and nitrates and aluminum halide and nitrate/zirconium complexes of the present invention may be made into an antiperspirant compositions with virtually any of the usual vehicles of formulations known in the art.

DETAILED DESCRIPTION OF THE INVENTION

The present methods are directed to the preparation of basic aluminum halides and nitrates which comprise a majority of aluminum species having a relative retention time corresponding to Band II of the Standard Basic Aluminum Chloride Size Exclusion Chromatogram. A Size Exclusion Chromatogram may be obtained for samples of basic aluminum compounds by injecting the compounds into standard high performance liquid chromatography (HPLC) equipment. For these determinations a Waters HPLC instrument was used with a U6K LC injector, a 6000 A solvent delivery system, a R401 differential refractometer and a 730 data module.

The chromatographic column was a Phenomenex column which was 25 cm long with an ID of 6.2 mm, a pore size of 60 Angstroms and a particle size of 5–7 microns.

Each sample was dissolved in deionized water to form a 2% w/w Al solution. Each sample was filtered through a 0.45 filter and chromatographed within 5 minutes. Samples of 10 microliters were used at a flow rate of 1.0 ml/min., at a pressure of 400–500 psig, at a chart speed of 2.0 cm/min., and 0.01N $HNO_3$ eluent.

The relative retention time for Band II of the Standard Basic Aluminum Chloride Size Exclusion Chromatogram for this equipment was determined to be 0.67 to 0.69. The relative retention time for Band I and Band III of the Standard Basic Aluminum Chloride Size Exclusion Chromatogram for this equipment was 0.64–0.65 and 0.71–0.73, respectively.

The basic aluminum halides and nitrates prepared in accordance with the present method comprise more than about 50%, and preferably about 70% to about 85%, of aluminum species having a relative retention time corresponding to Band II. Moreover, these compounds comprise less than 20% of aluminum species having a relative retention time corresponding to Band III. Preferably, these compounds further comprise less than 1% of aluminum species having a relative retention time corresponding to Band I.

The present method comprises reacting (a) aluminum powder, (b) an aluminum halide or nitrate solution and (c) water. Examples of the aluminum powder which may be used in the present method are metallic aluminum powders, such as Ampal Grade 601 and Alcan Grade 52R or 5238.

Generally, any standard aluminum halide or aluminum nitrate solution conventionally used in the art may be used in the present method. Such solutions generally have a solution solids concentration of about 28 wt. %. This corresponds to an aluminum content of about 5.7%. However, it will be evident to one skilled in the art that aluminum halide or nitrate solutions having other concentrations may also be used in the present method.

The three components of the present method (i.e., the aluminum powder, the aluminum halide or nitrate solution, and water) should be reacted at a temperature greater than about 85° C. Preferably, the components are reacted at a temperature of about 90° to about 95° C.

The reaction is maintained until a reaction product having an Al:anion ratio of about 1.2 to about 1.8 and a solution solids concentration of about 28 to about 42 wt. % on an anhydrous basis is obtained. Preferably, the reaction is maintained until reaction products having an Al:anion ratio of about 1.6 to about 1.7 and a solution solids concentration of about 35 to about 40 wt. % on an anhydrous basis are obtained, as such products reduce the probability of irritancy to the skin of human subjects. The correct Al:anion ratio and solution solids concentration are critical in obtaining reaction products having a Size Exclusion Chromatography Test Band having a relative retention time corresponding to Band II of the Standard Basic Aluminum Chloride Size Exclusion Chromatogram, a Band II Percent Aluminum Value of greater than about 50% and a Band III Percent Aluminum Value of less than 20%.

It has been discovered that when the Al:anion ratio of the reaction products is within the above-disclosed ranges, the majority of the aluminum species have a relative retention time corresponding to Band II and only a very small number of aluminum species have a relative retention time corresponding to Band III. Such products are advantageous as they provide excellent antiperspirant efficacy. The present inventors have also found that generally, solution solids concentrations lower than about 28% (on an anhydrous basis) result in the formation of more Band III species, while solution solids concentrations of about 28 to about 42 wt. % (on an anhydrous basis) result in a preponderance of Band II species.

Once the desired reaction products are obtained, the products may be cooled, filtered and then dried by any appropriate means known to those skilled in the art. However, preferably the reaction products are spray dried to powder form.

The basic aluminum halides and nitrates of the present invention may also be prepared by an "indirect" process which comprises taking a conventional 5/6 basic aluminum halide or nitrate solution having an Al:anion ratio of about 1.9 to 2.1 (e.g., "Chlorhydrol" by Reheis Inc.) and adjusting the Al:anion ratio of the solution to about 1.2 to 1.8 by adding an appropriate amount of hydrochloric acid or 32° Be (approximately 28 wt. %) aluminum chloride or nitrate solution thereto. This adjusted composition is then refluxed for about 2 to about 6 hours and preferably 4 hours. The products of this process also comprise the desired Band II percentage (i.e., at least 50%) and less than 20% Band III aluminum species.

The present invention further comprises a method of preparing aluminum halide and nitrate/zirconium complexes. This method comprises reacting, at room temperature, a basic aluminum halide or nitrate solution prepared by the above method (i.e., having at least about 50% of aluminum species in Band II and less than 20% of aluminum species in Band III) with a zirconium compound, which is preferably buffered with an amino acid.

The zirconium compounds useful in the present invention include zirconyl chloride (also referred to as basic zirconium chloride or zirconium oxychloride) and zirconyl hydroxy chloride, which may be represented by the formulas $ZrOCl_2$ and $ZrO(OH)Cl$, respectively. These compounds are commercially available in solution form or may be prepared by dissolution of commercially available zirconium carbonate paste (carbonated hydrous zirconia) in the appropriate amount of the acid of the anion to be used, e.g., hydrochloric acid. A particularly preferred zirconium compound useful in the present method is a zirconium hydroxychloride trihydrate solution which comprises about 18.5 to 20% $ZrO_2$; about 4.8 to 6.3% Cl; and which has a Cl:Zr ratio of about 1.1:1 to 0.9:1.

The zirconium compounds are preferably buffered with an appropriate amount of an amino acid. Appropriate amino acid buffers useful in the present method are, e.g., the salts of neutral amino acids, i.e., amino acids in which the number of amino groups is equal to the number of carboxyl groups in the molecule. Examples of such amino acids include glycine (including alkaline and alkaline earth glycinates and aluminum magnesium hydroxy glycinate compounds), DL-valine, -alanine, arginine, L-proline and mixtures thereof. The preferred amino acid for use in the present method is glycine.

The zirconium/amino acid complex is prepared by refluxing a zirconium compound as described above with an appropriate amino acid for about 2 to about 6 hours and preferably about 4 hours, in order to form a reaction product. Once formed, this reaction product is reacted at room temperature with the basic aluminum halides and nitrates prepared by the method of the present invention as discussed above. The reaction product is then dried to powder form by any appropriate means, however, spray drying is preferred. Other methods for producing the same or similar zirconium/ amino acid complexes are disclosed in, e.g., U.S. Pat. Nos. 4,017,599; 4,028,390; 4,223,010; 3,981,986 and British Patent 1,353,915, the disclosures of which are incorporated herein by reference.

The reaction product of the zirconium/amino acid complex and the basic aluminum halide or nitrate solution prepared in accordance with the present method has an Al:Zr ratio of about 10:1 to about 1:10 and, preferably, about 3.3:1 to about 3.8:1.

The present invention will now be illustrated by reference to the following specific non-limiting examples.

PREPARATION EXAMPLES

Example 1

A basic aluminum chloride solution was prepared by reacting 183 grams of aluminum powder (99% min. purity, particle size 75% thru 325 mesh) with 740 grams of 32° Be aluminum chloride solution (i.e., approximately 28 wt. %) and 1327 grams of water at 90° to 95° C. until all of the aluminum metal was dissolved in the aluminum chloride solution. The resultant solution was filtered, spray dried and micronized.

The results of the chemical analysis of the resultant powder are set forth below:

| | |
|---|---|
| % Al | 24.8 |
| % Cl | 18.6 |
| pH 15% w/w solution | 3.9 |
| Al:Cl Ratio | 1.75 |
| Fe, ppm | 163 |
| % Band II (% Area) | 85.9 |

Example 2

An aluminum chloride zirconium amino acid complex was prepared by reacting the following components A and B at room temperature.

Component A was prepared by reacting 197 grams of metallic aluminum powder (99% minimum purity, particle size 75% minimum through 325 mesh) with 918 grams of 32° Be aluminum chloride solution (approximately 28 wt. %) and 885 grams of water at 90° to 95° C. The reaction was maintained until all of the aluminum was dissolved. The solution was then cooled and filtered.

The chemical analysis of component A showed the following:

| | |
|---|---|
| % Al | 11.6 |
| % Cl | 9.68 |
| Al:Cl Ratio | 1.58:1 |
| Fe, ppm | 17 |

Component B was prepared by refluxing 322 grams of glycine with 2,775 grams of zirconium hydroxy chloride trihydrate solution for 4 hours. The refluxed preparation was cooled at room temperature.

The components were combined at room temperature. The product of the reaction was then spray dried and micronized to below 10 micron particle size.

The chemical analysis of the aluminum chloride zirconium amino acid complex prepared in accordance with the above method is set forth below:

| HPLC Band II Percentage Area 54% Band II | |
|---|---|
| % Al | 14.6 |
| % Zr | 14.7 |
| Al:Zr Atomic Ratio | 3.42:1 |

-continued

| HPLC Band II Percentage Area 54% Band II | |
| --- | --- |
| % Cl | 18.2 |
| Metals:Cl Ratio | 1.36:1 |
| % Glycine | 10.5 |
| Particle Size (% through 10 micron mesh) | 98.8 |

Example 3

An aluminum chloride zirconium amino acid complex in accordance with the present invention was prepared by blending components A and B set forth below.

Component A was prepared by reacting 392 grams of aluminum powder (99% min. purity, particle size 75% thru 325 mesh) with 1,886 grams of 32° Be aluminum chloride solution (approximately 28 wt. %) and 1,722 grams of water at 90° to 95° C. until all of the aluminum was dissolved. The resultant solution was cooled and filtered. The chemical analysis of the resultant solution showed the following:

| % Al | 12.3 |
| --- | --- |
| % Cl | 10.0 |
| Al:Cl Ratio | 1.62:1 |

Component B was prepared by refluxing 2,776 grams of zirconium hydroxychloride trihydrate solution (15% Zr and 6.66% Cl) was 418 grams of glycine for 4 hours. The resultant solution was cooled to room temperature.

Components A and B were then combined at room temperature. The reaction product was then spray dried and micronized.

The reaction product of components A and B had the following chemical analysis:

| HPLC Band II Percentage Area 54% Band II | |
| --- | --- |
| % Al | 14.2 |
| % Zr | 14.5 |
| Al:Zr Ratio | 3.37 |
| % Cl | 17.2 |
| Metals:Cl Ratio | 1.41:1 |
| % Glycine | 14.5 |
| Particle Size (% through 10 micron mesh) | 87 |

Comparative Example

Example 4

In this example, six basic aluminum chlorides with various aluminum to chloride molar ratios (i.e., about 0.9 to 2) were prepared in accordance with the method of the present invention and their HPLC patterns were evaluated. The Al:Cl molar ratio of each sample is set forth in Table I below.

Each sample was analyzed for % Al, % Cl and HPLC pattern. The results are set forth in Table I. The relative retention times are based on the HCl peak. A small unassigned peak was noted at a relative retention time of 1.12, but was never more than 2% of the total intensity. The results are set forth in Table I:

TABLE I

| | Rel. Retention | | | | |
| --- | --- | --- | --- | --- | --- |
| Al/Cl | 0.64–0.65 | 0.67–0.69 | 0.71–0.73 | 0.79–0.84 | 1.00 |
| 0.979 | — | 28.2 | 24.7 | 33.8 | 13.3 |
| 1.218 | — | 59.2 | 9.2 | 24.4 | 7.2 |
| 1.449 | — | 77.9 | * | 15.8 | 6.3 |
| 1.682 | — | 71.2 | 15.1 | 8.5 | 5.1 |
| 1.723 | — | 77.7 | 12.2 | 6.2 | 3.9 |
| 1.962 | 27.3 | 55.0 | 13.6 | 4.1 | |

*shoulder to larger peak

As can be seen from Table I, a preponderance of Band II species occurs when the Al:Cl atomic ratio of the basic aluminum chloride is 1.2 or more. Moreover, when the Al:Cl ratio is within 1.2 to 1.8, the amount of Band III species is less than 20% and the amount of Band I species is less than 1%.

As can further be seen from Table I, a preponderance of Band II species (i.e., 55%) is seen even when the Al:Cl atomic ratio is as high as 1.962. However, when the Al:Cl atomic ratio is this high, Band I species begin to appear. Since aluminum species having a relative retention time corresponding to Band I are less efficacious than those having retention times corresponding to Band II, the use of basic aluminum chlorides having Al:Cl atomic ratios greater than about 1.8 are less advantageous than those having an Al:Cl atomic ratio between 1.2 and 1.8. Moreover, it can be seen that basic aluminum chlorides prepared in accordance with the present method have a low percentage of Band III species, regardless of the Al:Cl molar ratio used.

Example 5

The basic aluminum chloride solution prepared in Example 1 and an aluminum zirconium tetrachlorohydroxy glycine complex prepared in accordance with the method of the present invention and as described below were tested for antiperspirant efficacy.

The aluminum zirconium tetrachlorohydroxy glycine complex was prepared by reacting the following components A and B.

Component A was prepared by reacting 918 grams of 32° Be aluminum chloride with 187 grams of aluminum powder and 886 grams of water at 90°–95° C. The resultant reaction product had an Al:Cl ratio of 1.6.

Component B was prepared by refluxing zirconium hydroxychloride trihydrate solution with glycine for 4 hours. The reaction product was cooled to room temperature.

The components A and B were reacted at room temperature. This final reaction product solution was then spray dried to form a powder.

The basic aluminum compound prepared in Example 1 was spray dried to form a powder and then tested for efficacy by preparing a 25% aerosol formulation therewith. The aerosol comprised:

| 10% | Active Ingredient |
| --- | --- |
| 13.4% | Isopropyl Myristate |
| 0.8% | Bentone 38 |
| 0.8% | Alcohol, SDA-40 |
| 75.0% | Propellant A-46 (80% isobutane/20% propane) |

The powdered aluminum tetrachlorohydroxy glycine complex was tested for efficacy by preparing a 25% roll-on formulation therewith. The roll-on formulation comprised:

| | |
|---|---|
| 25% | Active Ingredient |
| 70.5% | Volatile Silicone |
| 2.7% | Bentone |
| 1.6% | SDA-40 |
| 0.2% | Deionized Water |

Each formulation was tested by an axillary antiperspirant study using 30 human volunteers at an independent laboratory (Hilltop Research Inc.).

The aerosol formulation containing the basic aluminum chloride prepared in accordance with the present method demonstrated a sweat reduction of 49.4%.

The roll-on formulation containing the aluminum halide/zirconium amino acid compound prepared in accordance with the present method demonstrated a sweat reduction of 74.6%.

Accordingly, from this data, it can be concluded that the basic aluminum chlorides of the present invention, which contain a preponderance of Band II aluminum species, are efficacious antiperspirants.

The present invention may be embodied in other specific forms without departing from the spirit or essential attributes thereof and, accordingly, reference should be made to the appended claims, rather than to the foregoing specification as indicating the scope of the invention.

We claim:

1. A method of preparing basic aluminum halides and nitrates comprising:

reacting (a) aluminum powder, (b) an aluminum halide or nitrate solution and (c) water, at a temperature greater than about 85° C., and maintaining this reaction until reaction products having an Al:anion ratio of 1.2 to 1.8 and a solution solids concentration of about 28 to about 42 wt. % on an anhydrous basis are obtained, said reaction products being characterized as having a Size Exclusion Chromatography Test Band having a relative retention time corresponding to Band II of a Standard Basic Aluminum Chloride Size Exclusion Chromatogram; and having a Band I percent aluminum value of less than 1%, a Band II percent aluminum value of greater than 50% and a Band III percent aluminum value of less than 20%.

2. A method as in claim 1, further comprising spray drying the reaction products.

3. A method as in claim 1, wherein said reaction is maintained until an Al:anion ratio of about 1.6 to 1.7 and a solution solids concentration of about 35 to 40 wt. % on an anhydrous basis is obtained.

4. A method as in claim 1, wherein said aluminum halide is aluminum chloride.

5. A method of preparing basic aluminum halide and nitrate/zirconium complexes comprising:

reacting, at room temperature, (1) a basic aluminum halide or nitrate solution prepared by the method comprising reacting (a) aluminum powder, (b) an aluminum halide or nitrate solution and (c) water, at a temperature greater than 85° C. and maintaining this reaction until reaction products having an Al:anion ratio of 1.2 to 1.8 and a solution solids concentration of about 28 to about 42 wt. % on an anhydrous basis are obtained, said reaction products being characterized as having a Size Exclusion Chromatography Test Band having a relative retention time corresponding to Band II of a Standard Basic Aluminum Chloride Size Exclusion Chromatogram; and having a Band I percent aluminum value of less than 1%, a Band II percent aluminum value of greater than 50% and a Band III percent aluminum value of less than 20%; and (2) a zirconium compound.

6. A method as in claim 5, wherein said zirconium compound is buffered with an amino acid by the method comprising refluxing a solution of said zirconium compound with an amino acid for about 2 to about 6 hours, to form a reaction product.

7. A method as in claim 5, further comprising spray drying said reaction products of (1) and (2).

8. A method as in claim 5, wherein said complex has an Al:Zr ratio of about 10:1 to 1:10.

9. A method as in claim 5, wherein said reaction of (a), (b) and (c) is maintained until a basic aluminum halide or nitrate solution having an Al:anion ratio of about 1.6 to about 1.7 and a solution solids concentration of about 35 to 40 wt. % on an anhydrous basis is obtained.

10. A method as in claim 5, wherein said aluminum halide is aluminum chloride.

* * * * *